United States Patent
Simanzhenkov et al.

(10) Patent No.: US 10,668,454 B2
(45) Date of Patent: *Jun. 2, 2020

(54) LOW PRESSURE GAS RELEASE HYDROTHERMAL AND PEROXIDE TREATMENT OF ODH CATALYST

(71) Applicant: NOVA Chemicals (International) S.A., Fribourg (CH)

(72) Inventors: Vasily Simanzhenkov, Calgary (CA); Xiaoliang Gao, Calgary (CA); David Jeffrey Sullivan, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/728,948

(22) Filed: Oct. 10, 2017

(65) Prior Publication Data

US 2018/0104675 A1   Apr. 19, 2018

(30) Foreign Application Priority Data

Oct. 18, 2016  (CA) ..................... 2945435

(51) Int. Cl.
*B01J 27/057* (2006.01)
*B01J 37/04* (2006.01)
(Continued)

(52) U.S. Cl.
CPC ......... *B01J 27/0576* (2013.01); *B01J 37/009* (2013.01); *B01J 37/03* (2013.01); *B01J 37/04* (2013.01); *B01J 37/06* (2013.01); *B01J 37/08* (2013.01); *B01J 37/10* (2013.01); *B01J 37/12* (2013.01); *C07C 5/48* (2013.01); *B01J 23/002* (2013.01); *B01J 2523/00* (2013.01); (Continued)

(58) Field of Classification Search
CPC ........ B01J 27/0576; B01J 37/04; B01J 37/08; C07C 2523/22; C07C 2523/28; C07C 2523/648; C07C 2523/652; C07C 2527/057; C07C 5/48
See application file for complete search history.

(56) References Cited

U.S. PATENT DOCUMENTS 4,618,593 A * 10/1986 Sasaki ................. B01J 27/0576
502/20
7,319,179 B2   1/2008 Lopez Nieto et al.
(Continued)

FOREIGN PATENT DOCUMENTS

WO    2009/106474 A2    9/2009
WO    WO-2015065241 A1 *  5/2015 ................ C01F 5/22

OTHER PUBLICATIONS

Xu (Chemistry of Zeolites and Related Porous Materials: Synthesis and structure, 2009 pp. 122-126).*
(Continued)

*Primary Examiner* — Jun Li
(74) *Attorney, Agent, or Firm* — Thomas J. Styslinger

(57) ABSTRACT

The preparation of an oxidative dehydrogenation catalyst comprising Mo, V, Nb and Te using a hydrothermal step. In some embodiments, the activity and reproducibility of the catalyst is improved by conducting the hydrothermal step while permitting gaseous products to leave the reactor. In some instances a condenser may be upstream of the outlet of the reactor.

15 Claims, 1 Drawing Sheet

(51) Int. Cl.
- *B01J 37/08* (2006.01)
- *B01J 37/12* (2006.01)
- *B01J 37/10* (2006.01)
- *B01J 37/00* (2006.01)
- *B01J 37/06* (2006.01)
- *C07C 5/48* (2006.01)
- *B01J 37/03* (2006.01)
- *B01J 23/00* (2006.01)

(52) U.S. Cl.
CPC ...... *C07C 2523/20* (2013.01); *C07C 2523/28* (2013.01); *C07C 2527/057* (2013.01); *Y02P 20/52* (2015.11)

(56) References Cited

U.S. PATENT DOCUMENTS

| | | | |
|---|---|---|---|
| 8,105,971 B2 | 1/2012 | Gaffney et al. | |
| 8,519,210 B2 | 8/2013 | Arnold et al. | |
| 2005/0239643 A1* | 10/2005 | Benderly | B01J 23/002 502/312 |
| 2012/0180389 A1* | 7/2012 | Knaebel | B01D 53/75 48/127.3 |
| 2014/0128653 A1 | 5/2014 | Bal et al. | |
| 2014/0155659 A1* | 6/2014 | Wendlinger | C07C 17/206 570/156 |
| 2014/0194642 A1* | 7/2014 | Endo | B01J 21/08 558/330 |
| 2016/0207035 A1* | 7/2016 | Zander | B01J 37/08 |
| 2016/0264868 A1* | 9/2016 | Gordon | C01F 5/22 |

OTHER PUBLICATIONS

Chu et al. (Performance of Phase-pure M1 MoVNbTeOx Catalysts by Hydrothermal Synthesis with Different Post-treatments for the Oxidative Dehydrogenation of Ethane, Applied Catalysis A:General 298 (2015) pp. 99-106).*

Lopez Nieto, J.M.; Botella, P; Vazquez, M.I. and Dejoz, A.; The selective oxidative dehydrogenation of ethane over hydrothermally synthesised MoVTeNb catalysts; Copyright The Royal Society of Chemistry, 2002; Chem. Commun., 2002, pp. 1906-1907.

Wen, C.Y. and Yu, Y.H.; Mechanics of Fluidization; Chemical Engineering Progress Symposium Series, vol. 62, (1966), pp. 100-111.

Peri, J.B. and Hensley, A.L. Jr.; The Surface Structure of Silica Gel, The Journal of Physical Chemistry; vol. 72, No. 8, Aug. 1968; pp. 2926-2933.

* cited by examiner

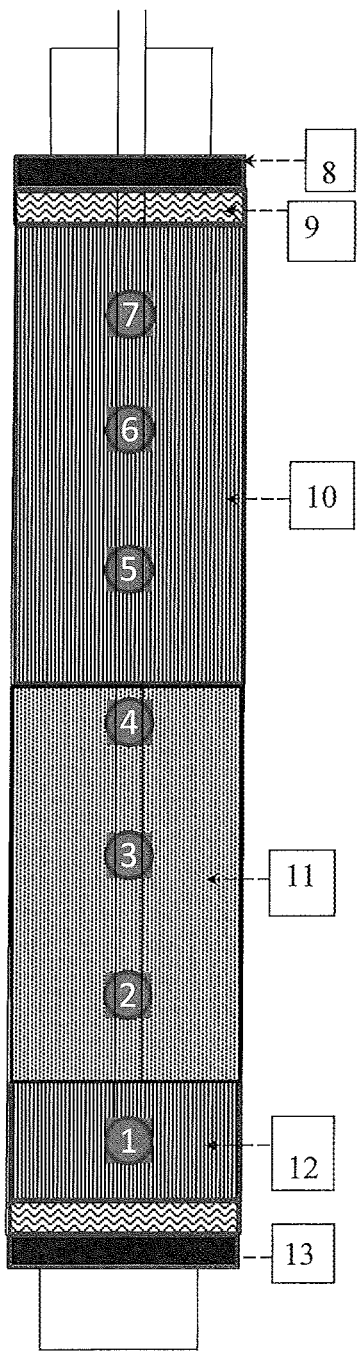

LOW PRESSURE GAS RELEASE HYDROTHERMAL AND PEROXIDE TREATMENT OF ODH CATALYST

The present disclosure relates to a process for the hydrothermal treatment of oxidative dehydrogenation catalysts (ODH) for lower alkanes. There are several methods to produce mixed oxide catalysts comprising Mo, V, Nb and Te suitable for use in the oxidative dehydrogenation of lower alkanes such as ethane to ethylene. One method uses a hydrothermal treatment of a slurry, suspension, gel or sol-gel of the mixed oxides. The resulting pre-catalyst is subjected to a number of treatments including drying and calcining to produce the final catalyst. A difficulty is that the hydrothermal treatment is variable and may produce catalysts having different reactivity.

There are a number of patents which teach conducting the hydrothermal process in an autoclave. Representative of such art are the following patents.

U.S. Pat. No. 7,319,179 issued Jan. 15, 2008 to Lopez Nieto et al., assigned to Consejo Superior De Investigaciones Cientificas, Universidad Politecnica De Valencia, teaches at Col. 4 lines 1-23 that the "mixing stage may be carried out in an auotoclave. In examples 5, 7, and 11 the hydrothermal treatment is carried out in an autoclave. The patent teaches the autoclave is kept at 175° C. static for a specified period of time. This teaches away from the subject matter disclosed herein.

U.S. Pat. No. 8,105,971 issued Jan. 31, 2012 to Gaffney assigned to Lummus Technology Inc. teaches at Col. 6 lines 6 and 7 that the admixing step may be carried out in an autoclave. No conditions are specified for the autoclave. The catalyst in the patent contains Sb and Ni which are absent from embodiments disclosed herein. There are no examples of conducting the hydrothermal treatment in an autoclave.

U.S. Pat. No. 8,519,210 issued Aug. 27, 2013 to Arnould et al., assigned to Lummus Technology Inc. contains the same teaching at Col. 6 lines 25 and 26. There are no examples of the hydrothermal treatment being carried out in an autoclave.

U.S. Patent Application Publication 2014/0128653 in the name of Bal et al., assigned to the Council of Scientific & Industrial Research, New Delhi teaches autoclaving the titanium support for an Mo catalyst for the oxidative dehydrogenation of ethane. This teaches away from the subject matter disclosed herein.

Published German patent application DE102013014241 teaches a MoVNbTe ODH catalyst which is prepared using a conventional hydrothermal treatment and subsequently treated with low pressure steam. This teaches away from the subject matter disclosed herein.

Published German Patent application DE112009000404 (WO2009/106474) teaches a process for treating a calcined an ODH catalyst prepared using a hydrothermal treatment. The catalyst is treated at a pressure of at least 10 MPa and a temperature of at least 400° C. in the presence of a fluid phase is at least one compound having a molecular weight of less than 150 and at least two different elements selected from C, S, O and H. Preferably the fluid is selected from $CO_2$, $H_2O$ and $SO_2$. This teaches away from the subject matter disclosed herein.

Interestingly paragraph 8 of DE112009000404 discloses the problem of reproducability of the catalyst in production of small scale laboratory procedures.

The paper "Selective oxidative dehydrogenation of ethane on MoVTeNbO mixed metal oxide catalysts" by P. Botella, E. Garcia-Gonzalez, A. Dejoz, J. M. Lopez Nieto, M. I. Vazquez and Gonzalez-Cabet Journal of Catalysis 225 (2004) 428-438, teaches hydrothermal treatment of various gels of the catalyst precursors. The examples of table 1 never attained a low Te loading. The example with a low Te loading has low conversion to ethylene. The catalysts disclosed herein have a higher conversion to ethylene.

In some embodiments, the present disclosure seeks to provide a process for the production of ODH catalysts using a hydrothermal treatment in which the activity of the catalyst is good and the consistency of the catalyst is improved.

In some embodiments, the present disclosure provides a process for synthesis of a catalyst for the oxidative dehydrogenation of paraffins via hydrothermal treatment comprising:

i) preparing an aqueous slurry (gel, sol-gel, dispersion, or suspension) comprising Mo, V, Nb and Te salts in a molar ratio: Mo 1:V 0.4 to 0.8, for example, 0.45 to 0.65, or for example, 0.50 to 0.60; Nb 0.15 to 0.25, for example, 0.15 to 0.20; and Te 0.15 to 0.25, for example, 0.15 to 0.20 at a temperature from 25° C. to 80° C., for example, 45° C. to 80° C.;

ii) boiling the slurry in a reaction vessel, (for example, with a heating medium (bath, sand, metal block, etc) controlled, to a temperature from 100° to 150° C., for example, from 120° C. to 150° C.), at a pressure up to 10 psig (68.9 kPag) above atmospheric pressures for a period of time not less than 21 hours, or for example, less than 75 hours, or for example, from 22 to 73 hours, with agitation and simultaneous removal of gaseous byproduct species produced during the reaction (hydrothermal treatment);

iii) letting the reactor cool and recovering, drying and calcining the solid product; and iv) treating the calcined product with the equivalent of from 0.3-2.8 mL, in some embodiments from 0.3-2.5 mL, of a 30 wt. % solution of aqueous $H_2O_2$ per gram of calcined catalyst precursor; and v) drying the treated catalyst.

The resulting catalyst has a reduced amount of Te and a higher content of Nb (relative to a calcined catalyst which has not been treated with hydrogen peroxide) and a 25% conversion of ethane to ethylene at temperatures less than 400° C.

In a further embodiment, the heating medium is heated to a temperature from 120° C.-150° C.

In a further embodiment, the pressure in the reactor is from 1 to 8 psig (6.89 kPag to 55.1 kPag), or for example, less than 5 psig (34.4 kPag) above atmospheric pressure.

In a further embodiment, optionally there is a condenser upstream of the reactor outlet.

In a further embodiment, the condenser is operated at a temperature above 0° C. and below reaction temperature.

In a further embodiment, the gaseous product species are vented from the reactor.

In a further embodiment, that pressure inside the reactor is maintained above atmospheric using a liquid filled column or bubbler.

In a further embodiment, the gaseous species are removed from the reactor using one or more methods selected from gas absorption, gas adsorption, membrane separation, and chemicals transformation.

In a further embodiment, the time of hydrothermal treatment is conducted from 21 to 75 hours.

In a further embodiment, the reactor is glass.

In a further embodiment, the reactor can contains glass fibers, beads, or other nucleating agents.

In a further embodiment, the aqueous slurry comprises Mo, V, Nb and Te salts in a molar ratio; Mo 1:V 0.45 to 0.65:Nb 0.15 to 0.20:Te 0.15 to 0.20.

In a further embodiment, the resulting precatalyst is separated from the aqueous phase and washed with (distilled) water or an aqueous oxalic acid solution and dried in an oven for not less than 6 hours at a temperature from 70° C. to 120° C.

In a further embodiment, optionally the dried precatalyst is ground to a size of less than 125 µm, for example.

In a further embodiment, the dried precatalyst is calcined in an inert atmosphere at a temperature from 200° C. to 650° C. for a time from 1 to 20 hours.

In a further embodiment, the calcined product is treated with the equivalent of from 2 to 2.5 mL of 30% $H_2O_2$ per 1 g of calcined product.

In a further embodiment, the calcined product comprises the following molar ratios: Mo1:V 0.12-0.19:Te 0.14-0.16:Nb 0.15 as determine by PIXE.

In a further embodiment, there is provided an oxidative dehydrogenation catalyst (before treatment with $H_2O_2$) having the empirical formula as measured by PIXE (Particle Induced X-Ray Emission analysis):

$$Mo_{1.0}V_{0.12-0.19}Te_{0.14-0.16}Nb_{0.15}O_d$$

where d is a number to satisfy the valence of the oxide

In a further embodiment, there is provided an oxidative dehydrogenation catalyst selected from the group of oxidative dehydrogenation catalysts comprising MoVNbTe having the empirical formula as measured by PIXE:

$$Mo_{1.0}V_{0.12-0.19}Te_{0.14-0.16}Nb_{0.15}O_d$$

where d is a number to satisfy the valence of the oxide.

The above compositions may come within the scope of broad disclosures of ODH catalysts comprising MoVNbTe in fact as far as Applicants can determine no one has produced a catalyst having such a low V (i.e. 0.12-0.19 content which increases upon treatment with $H_2O_2$). Further no one has produced a catalyst having the low Te (i.e. 0.06 to 0.07) and high Nb (i.e. 0.19 to 0.20) catalyst produced by treating the calcined catalyst with $H_2O_2$.

In a further embodiment, the calcined oxidative catalyst may comprise a 5th component selected from Sb, W, and Ni in amounts, for example, from 0.001 to 0.001 moles per mole of Mo.

In a further embodiment, the hydrogen peroxide treated product (calcined catalyst) comprises the following molar ratios: $Mo_1$:V 0.17-0.20:Te 0.06-0.07:Nb 0.19-0.20 as determine by PIXE. In a further embodiment there is provided a oxidative dehydrogenation catalyst having the empirical formula as measured by PIXIE:

$$Mo_{1.0}V_{0.17-0.20}Te_{0.06-0.07}Nb_{0.19-0.20}O_d$$

where d is a number to satisfy the valence of the oxide.

In a further embodiment, there is provided an oxidative dehydrogenation catalyst selected from the group of oxidative dehydrogenation catalysts comprising MoVNbTe having the empirical formula as measured by PIXE:

$$Mo_{1.0}V_{0.17-0.20}Te_{0.06-0.07}Nb_{0.19-0.20}O_d$$

where d is a number to satisfy the valence of the oxide.

In a further embodiment, there is provided a method for the oxidative dehydrogenation of a mixed feed comprising ethane and oxygen in a volume ratio from 70:30 to 95:5 and optionally one or more $C_{3-6}$ alkanes or alkenes and oxygenated species including CO and $CO_2$ at a temperature less than 385° C., a gas hourly space velocity of not less than 100 $hr^{-1}$, and a pressure from 0.8 to 7 atmospheres comprising passing said mixture over the above catalyst.

In a further embodiment, the ODH process has a selectivity to ethylene of not less than 90%.

In a further embodiment, the gas hourly space velocity of the ODH process is not less than 500 $hr^{-1}$ desirably not less than 1500 $hr^{-1}$ in some embodiments 3000 $hr^{-1}$.

In a further embodiment, the temperature of the ODH process is less than 375° C., or for example, less than 360° C.

In a further embodiment, the catalyst in the ODH process forms a fixed bed.

BRIEF DESCRIPTION OF THE DRAWINGS

FIG. 1 is a schematic drawing of the reactor used for the testing the ODH catalysts.

NUMBERS RANGES

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, the amounts of the components actually used will conform to the maximum of 100 percent.

In the specification, the phrase the temperature at which there is 25% conversion of ethane to ethylene is determined by plotting a graph of conversion to ethylene against temperature typically with data points below and above 25% conversion or the data is fit to an equation and the temperature at which there is a 25% conversion of ethane to ethylene is determined. In some instances in the examples the data had to be extrapolated to determine the temperature at which 25% conversion occurred.

In the specification, the phrase selectivity at 25% conversion is determined by plotting the selectivity as function of temperature or fit to an equation. Then having calculated the temperature at which 25% conversion occurs one can determine either from the graph or from the equation the selectivity at that temperature.

Calcined product from a hydrothermal treatment process prepared and disclosed herein typically have the formula: $Mo_{1.0}V_{0.12-0.19}Te_{0.14-0.16}Nb_{0.15}O_d$ as determined by PIXE where d is a number to satisfy the valence of the oxide.

Hydrogen Peroxide treated catalysts prepared and disclosed herein typically have the formula: $Mo_{1.0}V_{0.17-0.20}Te_{0.06-0.07}Nb_{0.19-0.20}O_d$ where d is a number to satisfy the valence of the oxide.

The catalyst may optionally further comprise components such as Sb, W, Pd or Ni in very small amounts, for example, from 0.001 to 0.001 moles per mole of Mo. The fifth component may be incorporated by adding water soluble/dispersable salts to the slurry phase or by doping the resulting catalyst with a salt of the compound.

The starting composition to be treated in accordance with this disclosure may be prepared by a number of processes.

In one embodiment, precursor is prepared by mixing solutions or slurries (suspensions) of oxides or salts of the metallic components.

In another embodiment, the precursor may be prepared by a process comprising the following steps:

i) forming an aqueous solution of ammonium heptamolybdate (tetrahydrate) and telluric acid at a temperature from 30° C. to 85° C., in some embodiments from 45° C. to 80° C. and adjusting the pH of the solution to 6.5 to 8.5, or for example, from 7 to 8, or for example, from 7.3 to 7.7, in some embodiments with a nitrogen-containing base to form soluble salts of the metals;

ii) preparing an aqueous solution of vanadyl sulphate at a temperature from room temperature to 80° C. (for example, 45° C. to 70° C., or for example, 55° C. to 65° C.);

iii) mixing the solutions from steps i) and ii) together;

iv) slowly (dropwise) adding a solution of niobium monoxide oxalate ($NbO(C_2O_4H)_3$) to the solution of step iii) to form a slurry (sometimes also referred to as a gel or sol-gel or a dispersion or suspension).

The slurry comprises Mo, V, Nb and Te salts in a molar ratio of metal elements Mo 1:V 0.4 to 0.8 Nb 0.15 to 0.25; and Te 0.15 to 0.25. In some embodiments the aqueous slurry has a molar ratio Mo, V, Nb and Te salts 1:0.45 to 0.65:0.15 to 0.20:0.15 to 0.20.

The slurry is heated in a reactor using a heating media (bath, sand, metal, etc.) controlled to a temperature from 100° C. to 150° C., in some instances from 125° C. to 150° C., at a pressure slightly above atmospheric (1-10 psig) for a period of time not less than 21 hours, with agitation and simultaneous removal of gaseous byproduct species produced during the hydrothermal process.

The pressure in the reaction reactor may be up to about 10 psig (68.9 kPag), or for example, from 1 to 8 psig (6.89 kPag to 55.1 kPag), in some embodiments less than 5 psig (34.4 kPag) above atmospheric pressure. The reaction temperature may be from 90° C.-110° C. In some embodiments, the reaction time should be greater than 21 hours, for example, from 21 to 75 hours, in some instances from 48 to 72 hours. The pressure may be maintained in the reactor by submerging the vent line in a column of liquid to create a bubbler that maintains pressure on the reactor. The pressure in the reactor can be controlled by varying the height of the liquid or using a more or less dense liquid. The liquid could be selected from mercury, aqueous ammonium paratungstate, silica oil, heavy syrup, etc. Other liquids would be known to those skilled in the art. In some instances the pressure in the reactor could be controlled by a low pressure regulator.

In some embodiments, there may be a condenser upstream from the adjustable pressure relief valve. Generally the condenser is operated at a temperature above 0° C. and below reaction temperature. At these temperatures the condenser will not condense gaseous reaction by products such as CO, $CO_2$ $SO_2$, $SO_3$ and $NH_3$. The release of these gaseous by products promotes the formation of the more active catalyst, with significantly shorter hydrothermal reaction treatments than possible using the previously reported art of hydrothermal reaction treatment using a sealed reactor vessel. The condenser, if present, may be air or water cooled.

In some embodiments, the gaseous by products are vented from the reactor. In some cases the gaseous by products are removed from the reactor using one or more methods selected from gas absorption, gas adsorption, membrane separation, and chemicals transformation. Example gas adsorbents include carbon black and zeolites.

In some embodiments, the reactor is any suitable material which will not result in contamination of the slurry (e.g. rust or any element from the reactor). The reactor may contain glass fibers, beads, or other nucleating agents. The nucleating agents may be irregular (such as flakes, granules, globules, filaments etc.) or regular (such as spheres, elliptical, rods (stirring bars), rectangular prisms (both right and non-right), pentagonal prisms, pyramids, etc.). The reactor may also be seeded with an ODH catalyst having a 25% conversion to ethylene at less than 385° C. and a selectivity to ethylene of not less than 90%, for example, greater than 97%, or for example, greater than 98%. The seed catalyst loadings may range from 1 to 15 wt. % of the surface of the reactor (e.g. steel, TEFLON or FEP). If both inert seed particles and catalyst are used to seed the reactor the seed catalyst loadings relative to the particulates may range from 1 to 15 wt. % of the particulates.

After the reaction is completed, the reactor is cooled. The resulting precatalyst is separated from the aqueous phase, for example, by filtration or evaporation, and washed with (distilled or deionized) water or a (dilute) aqueous oxalic acid solution and dried in an oven for not less than 6 hours at a temperature from 70° C. to 120° C. The precatalyst may be dried in an atmosphere of one or more inert gases or the atmosphere may contain oxygen (e.g. air). In some instances optionally, the dried precatalyst may be ground using mechanical means (e.g. a ball or roller mill) or the dried precatalyst could be subject to cryogenic grinding. The dried and ground precatalyst may in some instances be subject to sieving through a small particle size sieve to obtain a fraction having a particle size less than 250 microns, or for example, less than 125 microns.

The resulting dried and optionally ground and sized precatalyst is then calcined. The catalyst precursor may be calcined in an inert atmosphere at a temperature from 200° C. to 600° C. for a time from 1 to 20 hours. The purge gases used for calcining are inert gases, including one or more of nitrogen, helium, argon, $CO_2$ (for example high purity>90%), said gases or mixture containing less than 1 vol. % hydrogen or air, at 200-600° C., or for example, at 300-500° C. The calcining step may take from 1 to 20 hours, in some instances from 5 to 15 hours in other instances from about 8 to 12 hours, for example, about 10 hours. The resulting mixed oxide catalyst is a friable solid typically insoluble in water. In some embodiments the calcined product has a bulk density from 1.20 to 1.53 g/cc. This bulk density is based on how much 1.5 mL of pressed and crushed catalyst weighs.

The calcined catalyst product is a dry friable product typically insoluble in water. If required the catalyst may be subject to a sizing step, such as grinding, to produce a desired particle size. Depending on how the catalyst is to be used the particle size may be different. For example for spray drying with a support the particle size may range from about 5 to 75 µm, in some cases from 10 to 60 µm. For use in a bed in unsupported form the particles may have a size from about 0.1 to 0.5 mm in some instances from 0.2 to 0.4 mm.

The calcined catalyst is treated with the equivalent of from 0.3-2.8, in some embodiments from 0.3-2.5 mL of a 30 wt. % solution of aqueous $H_2O_2$ per gram of calcined catalyst precursor. The treatment should be in a slurry (e.g. the precursor is at least partially suspended) to provide an even distribution of $H_2O_2$ and to control the temperature rise.

In some embodiments, the feed to the oxidative dehydrogenation reactor includes oxygen in an amount below the upper explosive/flammability limit. For example for ethane oxidative dehydrogenation, the oxygen will be present in an amount of not less than about 16 mole %, or for example, about 18 mole %, or for example from about 22 to 27 mole %, or for example, 23 to 26 mole %. It is desirable not to have too great an excess of oxygen as this may reduce selectivity arising from combustion of feed, final products, or both. Additionally, too high an excess of oxygen in the feed stream may require additional separation steps at the downstream end of the reaction.

To maintain a viable fluidized or moving bed, the mass gas flow rate through the bed must be above the minimum flow required for fluidization, for example from about 1.5 to about 10 times $U_{mf}$, or for example, from about 2 to about 6 times $U_{mf}$. $U_{mf}$ is used in the accepted form as the abbreviation for the minimum mass gas flow required to achieve fluidization, C. Y. Wen and Y. H. Yu, "Mechanics of Fluidization", Chemical Engineering Progress Symposium Series, Vol. 62, p. 100-111 (1966). The superficial gas velocity ranges from about 0.3 to about 5 m/s.

In some embodiments, the reactor may be a fixed bed reactor.

In some embodiments, the oxidative dehydrogenation (ODH) process comprises passing a mixed feed of ethane and oxygen at a temperature less than 420° C. in some instances less than 410° C., in some instances less than 400° C., in some instances less than 390° C., in some instances less than 380° C. The catalysts disclosed herein may be used at a gas hourly space velocity of not less than 500 hr$^{-1}$, or for example, not less than 1500 hr$^{-1}$, or for example at least 3000 hr$^{-1}$ through one or more fixed beds at a pressure from 0.8 to 1.2 atmospheres. In some embodiments the catalyst permits the oxidative dehydrogenation reactor to operate at temperatures, for example, from 375° C. to 400° C., in some instances from 340° C. to 360° C. at a space velocity from 500 hr$^{-1}$ to 3000 hr$^{-1}$.

The outlet pressure from the ODH reactor may be from 105 kPag (15 psig) to 172.3 kPag (25 psig) and the inlet pressure is higher by the pressure drop across the bed which depends on a number of factors including reactor configuration, particle size in the bed and the space velocity. The pressure drop may be below 689 kPag (100 psig) preferably less than 206.7 kPag (30 psig).

The residence time of one or more alkanes, for example, $C_{2-4}$ alkanes, in the oxidative dehydrogenation reactor is from 0.002 to 20 seconds.

The Support/Binder:

If required there are several ways the oxidative dehydrogenation catalyst may be supported or bound.

Example components for forming ceramic supports and for binders include oxides of titanium, zirconium, aluminum, magnesium, silicon, phosphates, boron phosphate, zirconium phosphate and mixtures thereof, for both fluidized and fixed bed reactors. In the fluidized bed in some embodiments catalyst is spray dried with the binder, forming, in some embodiments, spherical particles ranging in size (effective diameter) from 40-100 µm. However, one needs to be careful to insure that the particles are sufficiently robust to minimize the attrition in the fluidized bed.

The support for the catalyst for the fixed bed may further be a ceramic precursor formed from oxides, dioxides, nitrides, carbides selected from silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, yttrium oxide, aluminum silicate, silicon nitride, silicon carbide and mixtures thereof.

In one embodiment, the support for the fixed bed may have a low surface area less than 20 m$^2$/g, alternatively, less than 15 m$^2$/g, in some instances, less than 3.0 m$^2$/g for the oxidative dehydrogenation catalyst. Such support may be prepared by compression molding. At higher pressures the interstices within the ceramic precursor being compressed collapse. Depending on the pressure exerted on the support precursor the surface area of the support may be from about 20 to 10 m$^2$/g.

The low surface area support could be of any conventional shape such as spheres, rings, saddles, etc.

It is important that the support be dried prior to use (i.e. before adding catalyst). The support may be heated at a temperature of at least 200° C. for up to 24 hours, at a temperature, for example, from 500° C. to 800° C. for about 2 to 20 hours, or for example, 4 to 10 hours. The resulting support will be free of adsorbed water and should have a surface hydroxyl content from about 0.1 to 5 mmol/g of support, for example, from 0.5 to 3 mmol/g.

The amount of the hydroxyl groups on silica may be determined according to the method disclosed by J. B. Peri and A. L. Hensley, Jr., in *J. Phys. Chem.*, 72 (8), 2926, 1968, the entire contents of which are incorporated herein by reference.

The dried support for a fixed bed catalyst may be compressed into the required shape by compression molding. Depending on the particle size of the support, it may be combined with an inert binder to hold the shape of the compressed part.

Loadings

In some embodiments the catalyst loading on the support for a fixed bed catalyst provides from 1 to 30 weight %, or for example, from 5 to 20 weight %, or for example, from 8 to 15 weight % of said catalyst and from 99 to 70 weight %, or for example, from 80 to 95 weight %, or for example, from 85 to 92 weight %, respectively, of said support.

The catalyst may be added to the support in any number of ways. For example the catalyst could be deposited from an aqueous slurry onto one of the surfaces of the low surface area support by impregnation, wash-coating, brushing or spraying. The catalyst could also be co-precipitated from a slurry with the ceramic precursor (e.g. alumina) to form the low surface area supported catalyst.

The catalyst loading for the fluidized bed may be chosen based on a number of factors including the volume of bed, the flow rate of alkane through the bed, energy balance in the bed, binder type, etc. For the fluidized bed catalyst loading may cover a wide range of values ranging from 10 wt. % up to 90 wt. %, or for example, above 20 wt. %, or for example, above 35 wt. %.

The process should be operated to have a conversion of ethane to ethylene of at least 90%, in some instances 95%, in some instances greater than 98% and a selectivity to ethylene of not less than 95%, in some instances greater than 97%.

The Oxidative Dehydrogenation Processes

The catalyst may be used with a fixed bed or a fluidized bed exothermic reaction. The fixed bed reactor is a tubular reactor and in further embodiment the fixed bed reactor comprises multiple tubes inside a shell (e.g. a shell and tube heat exchanger type construction). In a further embodiment the fixed bed reactor may comprise a number of shells in series and/or parallel. The reactions may involve one or more dehydrogenation steps including oxidative dehydrogenation, and hydrogen transfer steps including oxidative coupling of a hydrocarbon.

In some embodiments, these reactions are conducted at temperatures from about 375° C. up to about 410° C., at pressures from about 100 to 21,000 kPag (15 to 3000 psig), at an outlet pressure, for example, from 105 kPag (15 psig) to 172.3 kPag (25 psig), in the presence of an oxidative dehydrogenation catalyst. The hydrocarbon stream may contain a range of compounds including $C_{2-4}$ aliphatic hydrocarbons.

The resulting product stream is treated to separate ethylene from the rest of the product stream which may also contain co-products such as acetic acid, and un-reacted feed which is recycled back to the reactor.

Separation

The feed and by products may need to be separated from the product stream.

Some processes may use so called dilute ethylene streams. For example if the product stream does not contain too much ethane, for example less than about 15 vol. % the stream may be used directly without further purification in a polymerization reactor such as a gas phase, slurry or solution process.

The most common separation technique would be to use a cryogenic C2 splitter.

Other known ethylene/ethane separation techniques could also be used including adsorption (oil, ionic liquids and zeolite).

The present invention will now be illustrated by the following non limiting examples.

EXAMPLES

In the examples, the fixed bed reactor unit used for the oxidative dehydrogenation reaction is schematically shown in FIG. 1. The reactor was a fixed bed stainless steel tube reactor having a 2 mm (¾") outer diameter and a length of 117 cm (46 inches). The reactor is in an electrical furnace sealed with ceramic insulating material. There are 7 thermocouples in the reactor indicated at numbers 1 through 7. Thermocouples are used to monitor the temperature in that zone of the reactor. Thermocouples 3 and 4 are also used to control the heating of the reactor bed. The feed flows from the top to the bottom of the reactor. At the inlet there is a ceramic cup 8 to prevent air drafts in the reactor. Below the ceramic cup is a layer of quartz wool 9. Below the layer of quartz wool is a layer of catalytically inert quartz powder. Below the quartz powder is the fixed bed 10 comprising catalyst. Below the fixed bed is a layer of quartz powder 11, a layer of quartz wool 12 and a ceramic cup 13. At the exit of the bed was a gas analyzer to determine the composition of the product stream. The GHSV was 2685 $hr^{-1}$ and the pressure was ambient.

For the examples, the bed temperature was taken as an average of the temperatures from thermocouples 2, 3 and 4. The feed stream was assumed to have the same temperature as the bed.

COMPARATIVE EXAMPLES

Example 1: Classic Slurry Method

Reaction (Reagents, Mols, Stoichiometry, Solvent, Reaction Time, Etc.):
$(NH_4)_6Mo_6TeO_{24}.xH_2O$: 6.4 g
$VOSO_4.3.47H_2O$: 3.4 g
$H_3[NbO(C_2O_4)_3]$: 4.56 mmols, 15.82 g of stock solution (0.2882 mmol Nb/g solution)
20 ml of distilled water was added to a 100 mL round bottomed flask containing $(NH_4)_6Mo_6TeO_{24}.xH_2O$ (6.4 g) and a stir bar. The slurry dissolved with the aid of a warm water bath (~60° C.).
8 mL of distilled water was added to a 50 mL beaker containing $VOSO_4.3.47H_2O$ (3.4 g). The blue solid dissolved with the aid of the warm water bath.

Both solutions were cooled to room temperature. The $VOSO_4$ solution was added slowly to the $(NH_4)_6Mo_6TeO_{24}.xH_2O$ solution. The beaker was rinsed with water (2×1 mL) and the rinsed solution was added to the flask. The colorless solution became brown, which was stirred for about 10 minutes under nitrogen.

The $H_3[NbO(C_2O_4)_3]$ solution was added dropwise to above solution with a pipette. A dull-pink slurry formed.

The slurry was evaporated with a slow nitrogen flow while the flask was stirred and placed in a 130° C. silicon oil bath. The color of the slurry turned to grey in about 30 minutes. The bath temperature was raised to 150° C. to drive off the solvent. The flask was then placed in an oven. Temperature was raised from room temperature to 230° C. and kept at 230° C. for 3.3 hours. The flask was cooled to room temperature. The solid was ground, sieved with a 250 μm sieve (9.16 g) and was calcined (O2 level in N2: 0.14 ppm). The black catalyst weighed 6.89 g.

Example 2: Classic Slurry Method as Described in the Literature, Modified by Water Wash Prior to Calcination Reaction (Reagents, Mols, Stoichiometry, Solvent, Reaction Time, Etc.):
$(NH_4)_6Mo_6TeO_{24}.xH_2O$: 6.4 g
$VOSO_4.3.47H2O$: 3.4 g
$H_3[NbO(C_2O_4)_3]$: 4.56 mmols, 15.82 g of stock solution (0.35186 mmol Nb/g solution)
20 ml of distilled water was added to a 100 mL round bottomed flask containing $(NH_4)_6Mo_6TeO_{24}.xH_2O$ (6.4 g) and a stir bar. The slurry dissolved with the aid of a warm water bath (~60° C.).
8 mL of distilled water was added to a 50 mL beaker containing $VOSO_4.3.47H_2O$ (3.4 g). The blue solid dissolved with the aid of the warm water bath.

Both solutions were cooled to room temperature. The $VOSO_4$ solution was added slowly to the $(NH_4)6Mo_6TeO_{24}.xH_2O$ solution. The beaker was rinsed with water (2×1 mL) and the rinsed solution was added to the flask. The colorless solution became brown, which was stirred for about 10 minutes under nitrogen.

The $H_3[NbO(C_2O_4)_3]$ solution was added dropwise to above solution with a pipette. A dull-pink slurry formed.

The slurry was evaporated with a slow nitrogen flow while the flask was stirred and placed in a 130° C. silicon oil bath. The color of the slurry turned to grey in about 30 minutes. The bath temperature was raised to 150° C. to drive off the solvent. The flask was then placed in an oven. Temperature was raised from room temperature to 230° C. and kept at 230° C. for 3.3 hours. The flask was cooled to room temperature. The solid was ground, sieved with a 250 μm sieve (9.16 g), washed with distilled water (500 mL) and was calcined ($O_2$ level in N2: 0.14 ppm). The black powder weighed 6.89 g.

Example 3: Reflux Method with 6 Reaction Time (Hydrothermal Method)

Reaction (Reagents, Mols, Stoichiometry, Solvent, Reaction Time, Etc.):
$(NH_4)6Mo_6TeO_{24}.xH2O$: 6.4 g
$VOSO_4.3.47H2O$: 3.4 g
$H_3[NbO(C_2O_4)_3]$: 4.56 mmols, 12.96 g of stock solution (0.35186 mmol Nb/g solution)
Detailed Description of Prep:
20 ml of distilled water was added to a 100 mL round bottomed flask containing $(NH_4)6Mo_6TeO_{24}.xH2O$ (6.4 g) and a stir bar. The slurry dissolved with the aid of a warm water bath (~60 C).
8 mL of distilled water was added to a 50 mL beaker containing $VOSO_4.3.47H2O$ (3.4 g). The blue solid dissolved with the aid of the warm water bath.

Both solutions were cooled to room temperature. The $VOSO_4$ solution was added slowly to the $(NH_4)6Mo_6TeO_{24}.xH2O$ solution. The beaker was rinsed with water (2×1 mL) and the rinsed solution was added to the flask.

The colorless solution became brown, which was stirred for about 10 minutes under nitrogen.

The $H_3[NbO(C_2O_4)_3]$ solution was added dropwise to above solution with a pipette. A dull-pink slurry formed. The flask was fit with a condenser (while air was carefully purged out) and a slow flow of nitrogen was passed over the top of the condenser to a water bubbler. The mixture was stirred at 320 rpm and refluxed with an air cooled condenser at a bath temperature of 150° C. for 6 hours. The color of the reaction slurry changed from purple to green tint to light grey to purple. The solid was filtered, washed with about 500 mL of distilled water and was dried at 90 C over a weekend. The solid was ground, sieved through a 250 μm sieve (5.62 g) and was calcined ($O_2$ level in $N_2$ 0.14 ppm) (RT to 600° C. in 6 hrs, and kept at 600° C. for 2 hrs under N2). The black solid was ground and sieved through a 250 μm sieve. The resulting black solid weighed 4.82 g.

Examples of a low back pressure (i:e. water bubbler) longer term treatment Example 4-73 hours reflux prepared catalyst with no $H_2O_2$ treatment:
Reaction (Reagents, Mols, Stoichiometry, Solvent, Reaction Time, Etc.):
$(NH_4)6Mo_6TeO_{24}.xH_2O$: 6.4 g
$VOSO_4.3.47H_2O$: 3.4 g $H_3[NbO(C_2O_4)_3]$: 4.56 mmols, 13.33 g of stock solution (0.3420 mmol Nb/g solution)
Detailed Description of Prep:
20 ml of distilled water was added to a 100 mL round bottomed flask containing $(NH_4)6Mo_6TeO_{24}.xH2O$ (6.4 g) and a stir bar. The slurry dissolved with the aid of a warm water bath (~60 C).
8 mL of distilled water was added to a 50 mL beaker containing $VOSO_4.3.47H_2O$ (3.4 g). The blue solid dissolved with the aid of the warm water bath.

Both solutions were cooled to room temperature. The $VOSO_4$ solution was added slowly to the $(NH_4)6Mo_6TeO_{24}.xH_2O$ solution. The beaker was rinsed with water (2×1 mL) and the rinsed solution was added to the flask.

The colorless solution became brown, which was stirred for about 10 minutes under nitrogen.

The $H_3[NbO(C_2O_4)_3]$ solution was added dropwise to above solution with a pipette. A dull-pink slurry formed. The flask was fit with a condenser (while air was carefully purged out) and a slow flow of nitrogen was passed over the top of the condenser to a water bubbler. The height of the water in the bubbler was about 24 inches. The mixture was stirred at 320 rpm and refluxed with an air cooled condenser at a bath temperature of 150° C. for 75 hours. The solid was filtered, washed with about 700 mL of distilled water and was dried at 90° C. overnight. The solid was ground, sieved through a 250 μm sieve and was calcined as described above ($O_2$ level in N2: 0.14 ppm). The black solid was ground and sieved through a 250 μm sieve. The black solid weighed 5.7 g.

Example 5: 73 Hours Reflux Prepared Catalyst with No $H_2O_2$ Treatment and a Taller Water Bubbler (Increases Reactor Pressure)

$(NH_4)6Mo_6TeO_{24}.xH_2O$: 6.4 g
$VOSO_4.3.47H_2O$: 3.4 g
$H_3[NbO(C_2O_4)_3]$: 4.56 mmols, 15.82 g of stock solution (0.2882 mmol Nb/g solution)
Detailed Description of Prep: (Similar to Example 4, but Increased Water Height in Water Bubbler by about 4 Inches)
20 ml of distilled water was added to a 100 mL round bottomed flask containing $(NH_4)6Mo_6TeO_{24}.xH_2O$ (6.4 g) and a stir bar. The slurry dissolved with the aid of a warm water bath (~60° C.).
8 mL of distilled water was added to a 50 mL beaker containing $VOSO_4.3.47H_2O$ (3.4 g). The blue solid dissolved with the aid of the warm water bath.

Both solutions were cooled to room temperature. The $VOSO_4$ solution was added slowly to the $(NH_4)6Mo_6TeO_{24}.xH_2O$ solution. The beaker was rinsed with water (2×1 mL) and the rinsed solution was added to the flask.

The colorless solution became brown, which was stirred for about 10 minutes under nitrogen.

The $H_3[NbO(C_2O_4)_3]$ solution was added dropwise to above solution with a pipette. A dull-pink slurry formed. The flask was fit with a condenser (while air was carefully purged out) and a slow flow of nitrogen was passed over the top of the condenser to a water bubbler. The height of water in the bubbler was 4 inches. The mixture was stirred at 320 rpm and refluxed with an air cooled condenser at a bath temperature of 150° C. The dull pink slurry changed color to greenish grey to grey in about 1 hour. The grey colored slurry changed to purple slurry in the process of refluxing. The total reaction time was 73 hours. There was no obvious loss of water in the slurry during the reaction process. The solid was filtered, washed with about 400 mL of distilled water and was dried at 90° C. overnight (6.26 g). The solid was ground, sieved through a 250 μm sieve and was calcined ($O_2$ level in $N_2$: 0.14 ppm). The black solid was ground and sieved through a 250 μm sieve (5.60 g).

Example 6: 21 Hours Reflux Prepared Catalyst with No $H_2O_2$ Treatment and a Taller Water Bubbler (Increases Reactor Pressure)

Reaction (Reagents, Mols, Stoichiometry, Solvent, Reaction Time, Etc.):
$(NH_4)_6Mo_6TeO_{24}.xH_2O$: 6.4 g
$VOSO_4.3.47H_2O$: 3.4 g
$H_3[NbO(C_2O_4)3]$: 4.56 mmols, 15.82 g of stock solution (0.2882 mmol Nb/g solution)
Detailed Description of Prep:
The reaction procedure is as described above except the reaction time was reduced to 21 hours from 73 hrs.

Inventive Example 7—78 Hour Reflux Prepared Catalyst Followed by $H_2O_2$ Treatment of the Calcined Product Reaction (Reagents, Mols, Stoichiometry, Solvent, Reaction Time, Etc.):
$(NH_4)_6Mo_6TeO_{24}.xH_2O$: 6.4 g
$VOSO_4.3.47H_2O$: 3.4 g
$H_3[NbO(C_2O_4)_3]$: 4.56 mmols, 15.82 g of stock solution (0.2882 mmol Nb/g solution)

Detailed Description of Prep:
Same procedures was used as in example 5. The catalyst mixture was refluxed for 78 hours with a 24" water bubbler and a condenser at bath temp 150° C. No water loss was observed. The resulting solid was filtered, washed with water, and dried at 90° C. overnight (6.67 g). The solid was ground and sieved through a 250 μm sieve and was calcined as in example 5.

The calcined solid was loaded in a 500 mL round bottom flask. 100 mL of water was added and then 15 mL of 30% $H_2O_2$ was added (2.2.5 mL of 30% $H_2O_2$ per gram of catalyst). The slurry was stirred for 24 hrs at room temperature. The black slurry became blueish grey. The solid was too fine to filter. The slurry was centrifuged (10,000 rpm, 20 minutes), the solid was washed with 50 mL of water and centrifuged (repeated 3 times). The solid (4.25 g) was dried at 80° C. overnight. The solid was ground and sieved with a 250 μm sieve (4.20 g).

The catalysts were then tested in the reactor illustrated in FIG. 1. A sample of catalyst was loaded into the reactor and the conversion of ethane to ethylene was determined as a function of temperature and the selectivity to ethylene was also measured as a function of temperature. The conversion data was either plotted on graph or fitted to an equation. From this data one determines the temperature at which there is 25% conversion of ethane to ethylene. The selectivity data was either plotted on a graph of fit to an equation. From this plot or equation the selectivity at 25% conversion can be determined.

The date for the classic examples (1-2) and short term low pressure are set forth in table 1. The catalysts were quite poor and the data had to be extrapolated (linearly) to determine the 25% conversion and selectivity.

TABLE 1

| Classic Examples Short Term Low Pressure Activity | | | | | |
|---|---|---|---|---|---|
| Example 1 Classic Slurry Method as described in literature | | Example 2 Classic Slurry Method with a water wash | | Example 3 6 hr low pressure reflux | |
| Temperature (° C.) at which 25% Conversion is obtained | Selectivity at 25% Conversion | Temperature (° C.) at which 25% Conversion is obtained | Selectivity at 25% Conversion | Temperature (° C.) at which 25% Conversion is obtained | Selectivity at 25% Conversion |
| 444.0 | 95.0 | 465.0 | 94.0 | >500.0 | <<95.0 |

The low back pressure examples (4-6) and the inventive example low back pressure and $H_2O_2$ treatment are shown in Table 2

TABLE 2

| Example # | Sample IDs | Temp (° C.) at which 25% Conversion is reached | Selectivity @ 25% | Slurry composition | | | | | | | | PIXE (finished catalyst solids composition) | | | | | | | | |
|---|---|---|---|---|---|---|---|---|---|---|---|---|---|---|---|---|---|---|---|---|---|
| Example 4-6 | 4 | 400 | 96.3 | Mo | 1 | V | 0.52 | Te | 0.17 | Nb | 0.16 | Mo | 1 | V | 0.19 | Te | 0.16 | Nb | 0.15 |
| | 5 | 402 | 96.6 | Mo | 1 | V | 0.52 | Te | 0.17 | Nb | 0.16 | Mo | 1 | V | 0.16 | Te | 0.16 | Nb | 0.15 |
| | 6 | 399 | 96.9 | Mo | 1 | V | 0.52 | Te | 0.17 | Nb | 0.16 | Mo | 1 | V | 0.12 | Te | 0.14 | Nb | 0.15 |
| Example 7 | 7 | 360 | 98.7 | Mo | 1 | V | 0.52 | Te | 0.17 | Nb | 0.16 | Mo | 1 | V | 0.20 | Te | 0.07 | Nb | 0.20 |
| | 7 | 354 | 96.2 | Mo | 1 | V | 0.52 | Te | 0.17 | Nb | 0.16 | Mo | 1 | V | 0.17 | Te | 0.06 | Nb | 0.19 |

The data from the tables show that the classic methods produce a catalyst having a 25% conversion of ethane to ethylene at a temperature in the range of about 440° C. Using a low back pressure on a low pressure reactor produces a catalyst having a temperature at which 25% conversion is reached in the range of about 400° C. The catalysts disclosed herein (example 7) have a composition as determined by PIXIE in the range $Mo_1V_{0.17-0.20}Te_{0.06-0.07}Nb_{0.19-0.20}$. However when the low back pressure hydrothermal type process is used and the calcined catalyst is treated with hydrogen peroxide in accordance with the present disclosure the temperature at which 25% conversions is obtained is in the range of 355° C. to 360° C. This is a significant reduction in the temperature at which 25% conversion is reached. Further the Te content in the catalyst is significantly reduced and the Nb content of the catalyst increases.

What is claimed is:

1. A process for the synthesis of a catalyst for the oxidative dehydrogenation of ethane to ethylene via a hydrothermal treatment comprising:

providing an aqueous slurry comprising Mo, V, Nb, and Te salts at a temperature from 25° C. to 80° C., wherein:
the molar ratio of Mo to V is from 1:0.4 to 1:0.8,
the molar ratio of Mo to Nb is from 1:0.15 to 1:0.25, and
the molar ratio of Mo to Te is from 1:0.15 to 1:0.25;
heating the slurry in a reactor to a temperature from 100° C. to 180° C. at a pressure up to 10 psig (68.9 kPag) above atmospheric for a period of time not less than 21 hours with agitation and simultaneous removal of gaseous byproduct species to provide a precatalyst;
recovering, drying and calcining the precatalyst to provide a calcined catalyst precursor; and
treating the calcined catalyst precursor with an equivalent of 0.3 to 2.5 mL of 30% by weight of aqueous hydrogen peroxide solution per gram of the calcined catalyst precursor, wherein the calcined catalyst precursor is suspended in an aqueous slurry containing $H_2O_2$ evenly distributed thereof to obtain the catalyst.

2. The process according to claim 1, wherein the reactor is heated with a heating media and wherein the temperature is controlled from 120° C. to 150° C.

3. The process according to claim 2, wherein the pressure in the reactor is from 1 psig to 8 psig (6.89 kPag to 55.1 kPag).

4. The process according to claim 3, wherein the pressure in the reactor is maintained above atmospheric using a liquid filled column or bubbler.

5. The process according to claim 1, wherein the gaseous species are vented from the reactor.

6. The process according to claim 1, wherein the gaseous species are removed from the reactor using one or more methods selected from gas absorption, gas adsorption, membrane separation, and chemicals transformation.

7. The process according to claim 1, wherein the time of hydrothermal treatment is from 21 to 75 hours.

8. The process according to claim 7, wherein the reactor can be lined or contain glass fibers, beads, or other nucleating agents.

9. The process according to claim 1, wherein: the aqueous slurry comprising Mo, V, Nb and Te has
the molar ratio of Mo to V is from 1:0.4 to 1:0.8,
the molar ratio of Mo to Nb is from 1:0.15 to 0:0.2, and
the molar ratio of Mo to Te is from 1:0.15 to 1:0.20.

10. The process according to claim 9, further comprising separating the precatalyst from the aqueous phase and washing the precatalyst with distilled water or an aqueous oxalate solution and drying the precatalyst.

11. The process according to claim 10, further comprising grinding the dried precatalyst.

12. The process according to claim 11, wherein calcining the precatalyst comprises calcining the precatalyst in an inert atmosphere at a temperature from 200° C. to 650° C. for a time from 1 to 20 hours.

13. The process according to claim 12, wherein the calcined catalyst precursor has:
the molar ratio of Mo to V is from 1:0.17 to 1:0.2, as determined by PIXE;
the molar ratio of Mo to Te is from 1:0.06 to 1:0.07, as determined by PIXE; and
the molar ratio of Mo to Nb is from 1:0.19 to 1:20, as determined by PIXE.

14. A process according to claim 12, wherein the calcined catalyst precursor is treated with 2.25 mL of 30% $H_2O_2$ in water per 1 g of the calcined catalyst precursor.

15. The process according to claim 14 wherein the calcined catalyst precursor comprises the following molar ratios: Mol:V 0.12-0.19:Te 0.14-0.16:Nb 0.15 as determine by PIXE.

* * * * *